United States Patent [19]

Yamamoto et al.

[11] 4,209,640

[45] Jun. 24, 1980

[54] CATALYSTS FOR THE OXIDATION OF UNSATURATED ALDEHYDES

[75] Inventors: Haruhisa Yamamoto; Kiyomori Ooura, both of Takaoka, Japan

[73] Assignee: Nippon Zeon Co., Ltd., Tokyo, Japan

[21] Appl. No.: 7,764

[22] Filed: Jan. 29, 1979

[30] Foreign Application Priority Data

Feb. 3, 1978 [JP] Japan .................................. 53-11331

[51] Int. Cl.² ............................................. C07C 51/32
[52] U.S. Cl. .................................... 562/532; 260/413; 252/435; 252/437
[58] Field of Search ....................... 562/532, 534, 535; 260/413 N

[56] References Cited

U.S. PATENT DOCUMENTS 4,118,419  10/1978  Ishii et al. ............................. 562/534
4,136,110  1/1979  White et al. ......................... 562/532

FOREIGN PATENT DOCUMENTS 51-76217   7/1976  Japan .
51-108016  9/1976  Japan .
7602710    9/1976  Netherlands ............................. 562/532

*Primary Examiner*—Norman Morgenstern
*Assistant Examiner*—L. Hendriksen
*Attorney, Agent, or Firm*—Wenderoth, Lind & Ponack

[57] ABSTRACT

A novel catalyst expressed by the formula $$A_aB_bCe_cMo_dP_eO_f$$

wherein A represents at least one element selected from K, $R_b$, $C_s$ and Tl; B represents at least one element selected from Be, Sr, Zn, Pb, Sb, Bi, Cr, Ag, Ga, Y, Ge, Te, La, Nd and Sm; a, b, c, d, e and f are the number of the atoms of A, B, Ce, Mo, P and O, respectively; and when d is 12, a, b, c and e are independently 0.05 to 12, and f is the number of oxygen atoms which satisfies the valences of the other elements is provided. This catalyst, when used in a reaction for preparing unsaturated carboxylic acids by oxidizing unsaturated aldehydes in the vapor phase, exhibits superior catalytic activity and does not cause reduction in activity by impurities such as olefins.

5 Claims, No Drawings

CATALYSTS FOR THE OXIDATION OF UNSATURATED ALDEHYDES

This invention relates to novel catalysts for oxidation of unsaturated aldehydes, and a process for preparing unsaturated carboxylic acids with the use of said catalysts. More specifically, the invention concerns a process which comprises catalytically oxidizing unsaturated aldehydes in the vapor phase in the presence of a catalyst having superior catalytic activity and undergoing no reduction in activity by impurities such as olefins, thereby to prepare the corresponding unsaturated carboxylic acids.

In recent years, extensive studies have been made on a process which comprises catalytically oxidizing olefins such as propylene or isobutylene, or tert-butyl alcohol in the vapor phase using molecular oxygen to prepare the corresponding unsaturated aldehydes such as acrolein or methacrolein (hereinafter referred to as first stage oxidation; catalysts to be used in this reaction are called first stage oxidation catalysts), and a process which comprises further catalytically oxidizing these unsaturated aldehydes in the vapor phase using molecular oxygen to prepare the corresponding unsaturated carboxylic acids such as acrylic acid or methacrylic acid (hereinafter referred to as second stage oxidation; catalysts for use in this reaction are called second stage oxidation catalysts). As a result, a number of first stage oxidation catalysts and second stage oxidation catalysts have already been proposed. Their catalytic activity, however, is still not entirely satisfactory, and desire has been raised for the development of catalysts, especially second stage oxidation catalysts, which have better performances.

In the production of unsaturated carboxylic acids, a process involving the second stage oxidation using unsaturated aldehydes in the purified form and a process comprising the second stage oxidation of the reaction mixture obtained by the first stage oxidation without purifying the reaction mixture (hereinafter called the first stage-second stage continuous method) are both known. Since the latter process does not need such treating steps as the separation and purification of unsaturated aldehydes, it is advantageous in apparatus, operation and economy and is considered advantageous commercially as well. However, if the first stage-second stage continuous method is performed using known first stage oxidation catalysts and second stage oxidation catalysts, then the catalytic activity of the second stage oxidation catalysts (conversion of unsaturated aldehydes, and yield and selectivity of unsaturated carboxylic acids) is generally much inferior to that exhibited if the second stage oxidation alone is carried out under the same reaction conditions using purified unsaturated aldehydes. This tendency is conspicuous particularly in the production of methacrylic acid from isobutylene. This phenomenon is known to be caused by small amounts of tarry substances formed as by-products in the first stage oxidation, or small amounts of unsaturated hydrocarbons such as the unreacted isobutylene. Particularly the unsaturated hydrocarbons are known to cause the phenomenon.

No proposals, therefore, have yet been offered to enable methacrylic acid to be produced on a commercial scale by the first stage-second stage continuous method. To make such method feasible, it would be insufficient simply to increase the catalytic activity in the second stage oxidation, and it is required to develop novel second stage oxidation catalysts which do not deteriorate even in the presence of small amounts of by-products or the unreacted isobutylene contained in the first stage oxidation reaction mixture.

The object of the present invention is therefore to provide novel second stage oxidation catalysts which are free from the above-described drawbacks of so far known catalysts for oxidation of methacrolein, which have excellent catalytic activity and which undergo little deterioration by olefins, etc.

We have eagerly made studies and found that catalysts expressed by the general formula [I] shown below are very useful in attaining said object, and that the catalysts are also suitable as catalysts for oxidation of other unsaturated aldehydes such as acrolein.

Thus, the present invention provides catalysts for oxidation of unsaturated aldehydes, said catalysts being expressed by the general formula [I]

$$A_a B_b Ce_c Mo_d P_e O_f \qquad [I]$$

wherein A represents at least one element selected from K, Rb, Cs and Tl; B represents at least one element selected from Be, Sr, Zn, Pb, Sb, Bi, Cr, Ag, Ga, Y, Ge, Te, La, Nd and Sm; a, b, c, d, e and f are the number of the atoms of A, B, Ce, Mo, P and O, respectively; and when d is 12, a, b, c and e independently denote 0.05 to 12, and f denotes the number of oxygen atoms which satisfies the valences of the other elements.

Of the above catalysts, particularly preferred are those in which when d is 12, a, b, c and e are independently 0.1 to 8 and f is the number of oxygen atoms which satisfies the valences of the other elements. Also particularly preferred are those in which component B is Be, Zn, Sr, Pb, Sb, Bi or Cr.

Catalysts comprising four components—molybdenum, phosphorus, an alkali metal or thallium, and cerium—have been known heretofore. For example, Japanese Laid-Open Patent Publication No. 76217/76 discloses Mo-P-Cs-Ce type catalysts, and Japanese Laid-Open Patent Publication No. 108016/76 discloses Mo-P-K, Rb, Cs or Tl-Ce type catalysts.

The feature of the catalysts of the present invention is that they contain component B. Since component B is contained, the use of the catalyst of the present invention enables unsaturated carboxylic acids to be obtained from unsaturated aldehydes in high yields at high selectivities by a stable reaction under practical reaction conditions. Moreover, even if small amounts of unsaturated hydrocarbons are present in the starting gas containing methacrolein, reduction of the catalytic activity hardly occurs. As a result, it becomes possible to produce methacrylic acid by the first stage-second stage continuous method though such production has been considered impossible when using known catalysts. Further, the conventional catalysts have often had difficulty in reproducing their catalytic activity, while the catalysts of the present invention always exhibit good activity.

The catalysts for use in the process of the present invention can be prepared by the so-called evaporation to dryness method, coprecipitation method, etc. which are known in the art. The starting materials used in preparing the catalysts are, for example, salts such as ammonium salts, nitrates, and halides; free acids; acid anhydrides; poly-acids; oxides; heteropoly-acids containing molybdenum such as phosphomolybdic acid; and heteropoly-acid salts such as acid salts, ammonium salts and alkali metal salts of heteropoly-acids. Particularly preferred is the use as the starting materials of compounds such as heteropoly-acids or their acid salts, ammonium salts and alkali metal salts which are capable of forming complex compounds.

The so prepared catalyst composition is calcined at a temperature of 250° to 700° C., preferably 300° to 550° C. for several hours to several ten hours in air, a reducing atmosphere or the starting gas before it is used as a catalyst.

The state of presence of those respective elements, including oxygen, of the catalyst of the present invention which are exhibiting catalytic action is not entirely clear, but it is believed that these elements are not in the form of a mere mixture of their oxides. For instance, it has been observed that the X-ray diffraction pattern of a mixture of the oxides and the X-ray diffraction pattern of the catalyst of the present invention which is obtained by calcining said mixture are different totally from each other.

The catalyst of the present invention can be used as it is, but can also be used as deposited on a carrier of a suitable shape or as diluted with a carrier (diluent) in the form of a powder, sol or gel. The carrier may be any known carrier, examples of which include titanium dioxide, silica gel, silica sol, diatomaceous earth, silicon carbide, alumina, pumice, silica-alumina, bentonite, zirconia, graphite, refractories, and zeolite.

The starting unsaturated aldehydes for use in the process of the present invention are preferably acrolein and methacrolein. When the first stage-second stage continuous method is employed, it is preferred to use as the starting material the reaction mixture obtained by the first stage oxidation of propylene, isobutylene or tert-butyl alcohol. As a source of molecular oxygen, oxygen can be used alone, but industrially, air suits practical purposes, and if the first stage-second stage continuous method is employed, it is also possible to utilize the unreacted oxygen contained in the reaction mixture of the first stage oxidation.

A gas exerting no influence on the reaction, such as steam, nitrogen, carbon dioxide, helium, argon, or saturated hydrocarbon (e.g. methane, ethane, propane, butane, pentane, etc.) may be introduced as a diluent to the reaction system. Further, when the first stage-second stage continuous method is employed, the inclusion of the unreacted starting material (propylene, isobutylene, tert-butyl alcohol, oxygen, etc.), diluent, by-products and so forth that are contained in the reaction mixture of the first stage oxidation would substantially exercise no adverse influences on the reaction.

The concentration of the unsaturated aldehyde in the starting mixture is preferably in the range of 1 to 25% by volume. The ratio of the unsaturated aldehyde to oxygen is 1:0.1 to 25.0, preferably 1:0.1 to 20.0. The reaction temperature is 250° to 500° C., preferably, 300° to 450° C. The contact time (based on 0° C., 1 atmosphere) is 0.1 to 20 seconds, preferably, 0.5 to 15 seconds.

In the present invention, the reaction pressure is not a particularly important factor, and high pressures would be usable, but a pressure of about 1 to 10 atmospheres is suitable for practical use. The reaction apparatus can adopt a fixed bed, fluidized bed or moving bed, and the reaction product can be separated and purified by a known ordinary method.

The present invention will be described more concretely below with reference to examples, in which the conversion of the unsaturated aldehyde, and the yield and selectivity of the unsaturated carboxylic acid are defined as follows, the analyses having been all made by a gas chromatograph:

$$\text{Conversion (\%)} = \frac{\text{Unsaturated aldehyde reacted (mol)}}{\text{Unsaturated aldehyde supplied (mol)}} \times 100$$

$$\text{Yield (\%)} = \frac{\text{Unsaturated carboxylic acid formed (mol)}}{\text{Unsaturated aldehyde supplied (mol)}} \times 100$$

$$\text{Selectivity (\%)} = \frac{\text{Yield}}{\text{Conversion}} \times 100$$

In the catalysts shown in the examples, the indication of oxygen is omitted for simplification.

EXAMPLE 1

(I) Ammonium molybdate (212 g) was dissolved, with heating, in 300 ml of water. To the solution were added an aqueous solution of 23 g of 85% phosphoric acid dissolved in 50 ml of water and an aqueous solution of 20.2 g of potassium nitrate dissolved, with heating, in 200 ml of water, and the mixture was stirred. Then, 1.25 g of finely divided beryllium oxide and 8.61 g of finely divided cerium oxide, both obtained by decomposing beryllium nitrate and cerium nitrate, respectively, in a stream of air at 500° C. for 16 hours, were added, and the mixture was evaporated to dryness while vigorously stirring it. The resulting product was calcined for 16 hours in a muffle furnace held at 450° C., then pulverized, and sifted to a size of 4 to 8 mesh. The product so obtained was of the composition $Mo_{12}P_2Ce_{0.5}Be_{0.5}K_2$ [catalyst No. (1) in Table 1-1].

Similarly, catalysts Nos. (2) to (4) in Table 1-1 were prepared by using 29.5 g of rubidium nitrate, 39.0 g of cesium nitrate and 53.3 g of thallium nitrate, respectively, instead of potassium nitrate.

(II) Catalysts Nos. (5) to (16) in Table 1-1 were prepared by using, instead of beryllium oxide, predetermined amounts of strontium oxide, zinc oxide, tin oxide, antimony oxide, bismuth oxide and chromium trioxide, respectively, in finely divided form. Of these metallic oxides, antimony oxide and chromium trioxide were marketed articles and the other oxides were obtained by decomposing the nitrates of the respective metals in a stream of air at 500° C. for 16 hours.

(III) Control catalysts Nos. (C-1) to (C-13) shown in Table 1-2 were prepared by omitting the use of part of the starting materials in the methods of (I) and (II).

Next, 100 ml of the catalyst was charged into a stainless steel reaction tube having an inside diameter of 2.5 cm and a length of 60 cm, and heated to 350° C. over a metal bath. A feed gas consisting of methacrolein, $O_2$, $N_2$ and $H_2O$ in a molar ratio of 1:1.5:17.5:10 was passed through the catalyst layer for a contact time of 1.8 seconds (based on 0° C., 1 atmosphere) to perform the reaction. The results obtained are tabulated in Tables 1-1 and 1-2. The purity of the methacrolein used was 99.5% by weight.

Table 1-1

| Catalyst No. | | Composition of catalyst (atomic ratio) | Conversion of methacrolein (%) | Per-pass yield (selectivity) of methacrylic acid (%) |
|---|---|---|---|---|
| | (1) | $Mo_{12}P_2Ce_{0.5}Be_{0.5}K_2$ | 74.3 | 54.5 (73.4) |
| | (2) | $Mo_{12}P_2Ce_{0.5}Be_{0.5}Rb_2$ | 75.2 | 56.2 (74.7) |
| | (3) | $Mo_{12}P_2Ce_{0.5}Be_{0.5}Cs_2$ | 76.9 | 58.3 (75.8) |
| | (4) | $Mo_{12}P_2Ce_{0.5}Be_{0.5}Tl_2$ | 76.2 | 56.8 (74.5) |
| | (5) | $Mo_{12}P_2Ce_{0.5}Sr_{0.5}K_2$ | 72.6 | 50.9 (70.1) |
| Present | (6) | $Mo_{12}P_2Ce_{0.5}Sr_{0.5}Cs_2$ | 74.8 | 53.9 (72.1) |
| Inven- | (7) | $Mo_{12}P_2Ce_{0.5}Zn_{0.5}Rb_2$ | 72.4 | 50.9 (70.3) |
| tion | (8) | $Mo_{12}P_2Ce_{0.5}Zn_{0.5}Tl_2$ | 72.9 | 51.5 (70.6) |
| | (9) | $Mo_{12}P_2Ce_{0.5}Pb_{0.5}Rb_2$ | 72.5 | 52.8 (72.8) |
| | (10) | $Mo_{12}P_2Ce_{0.5}Pb_{0.5}Cs_2$ | 74.5 | 55.3 (74.2) |
| | (11) | $Mo_{12}P_2Ce_{0.5}Sb_{0.5}K_2$ | 71.4 | 49.7 (69.6) |
| | (12) | $Mo_{12}P_2Ce_{0.5}Bi_{0.5}Rb_2$ | 74.1 | 53.2 (71.8) |
| | (13) | $Mo_{12}P_2Ce_{0.5}Cr_{0.5}Rb_2$ | 79.6 | 59.6 (74.9) |
| | (14) | $Mo_{12}P_2Ce_{0.5}Bi_{0.5}K_{0.5}Cs_{1.5}$ | 77.5 | 59.4 (76.6) |
| | (15) | $Mo_{12}P_1Ce_{0.5}Sr_{0.5}Pb_{0.4}Cs_2$ | 75.7 | 57.1 (75.4) |
| | (16) | $Mo_{12}P_1Ce_{0.2}Pb_{0.2}Cr_{0.5}Cs_2$ | 81.7 | 63.0 (77.1) |

Table 1-2

| Catalyst No. | | Composition of catalyst (atomic ratio) | Conversion of methacrolein (%) | Per-pass yield (selectivity) of methacrylic acid (%) |
|---|---|---|---|---|
| | (C-1) | $Mo_{12}P_2Ce_{0.5}K_2$ | 61.4 | 37.1 (60.4) |
| | (C-2) | $Mo_{12}P_2Ce_{0.5}Rb_2$ | 64.7 | 40.5 (62.6) |
| | (C-3) | $Mo_{12}P_2Ce_{0.5}Cs_2$ | 65.4 | 41.8 (63.9) |
| | (C-4) | $Mo_{12}P_2Ce_{0.5}Tl_2$ | 65.9 | 40.2 (61.0) |
| | (C-5) | $Mo_{12}P_2Be_{0.5}Cs_2$ | 71.7 | 51.4 (71.7) |
| Con- | (C-6) | $Mo_{12}P_2Sr_{0.5}Cs_2$ | 61.3 | 35.8 (58.4) |
| trol | (C-7) | $Mo_{12}P_2Zn_{0.5}Tl_2$ | 65.7 | 31.6 (48.1) |
| | (C-8) | $Mo_{12}P_2Pb_{0.5}Rb_2$ | 50.1 | 34.1 (68.1) |
| | (C-9) | $Mo_{12}P_2Sb_{0.5}K_2$ | 68.2 | 28.3 (41.5) |
| | (C-10) | $Mo_{12}P_2Bi_{0.5}Rb_2$ | 61.6 | 35.0 (56.8) |
| | (C-11) | $Mo_{12}P_2Cr_{0.5}Rb_2$ | 70.6 | 45.8 (64.9) |
| | (C-12) | $Mo_{12}P_2Ce_{0.5}Be_{0.5}$ | 40.9 | 14.4 (35.2) |
| | (C-13) | $Mo_{12}Ce_{0.5}Be_{0.5}Cs_2$ | 50.1 | 18.2 (36.3) |

EXAMPLE 2

Catalysts Nos. (17) to (24) shown in Table 2 were prepared by following Example 1 except that various metallic oxides were used in place of the beryllium oxide employed in the preparation of the aforementioned catalyst No. (3). Of the various metallic oxides, silver oxide, gallium oxide, lanthanum oxide, neodymium oxide and samarium oxide were obtained by decomposing the nitrates of the respective metals in a stream of air at 500° C. for 16 hours, and yttrium oxide, germanium dioxide and tellurium dioxide were marketed articles.

Using the so prepared various catalysts, the reaction was performed in the same way as in Example 1. The results obtained are shown in Table 2.

Table 2

| Catalyst No. | | Composition of catalyst (atomic ratio) | Conversion of methacrolein (%) | Per-pass yield (selectivity) of methacrylic acid (%) |
|---|---|---|---|---|
| | (17) | $Mo_{12}P_2Ce_{0.5}Ag_{0.5}Cs_2$ | 76.1 | 52.8 (69.4) |
| Pre- | (18) | $Mo_{12}P_2Ce_{0.5}Ga_{0.5}Cs_2$ | 73.4 | 49.3 (67.2) |
| sent | (19) | $Mo_{12}P_2Ce_{0.5}Y_{0.5}Cs_2$ | 76.9 | 54.4 (70.7) |
| In- | (20) | $Mo_{12}P_2Ce_{0.5}Ge_{0.5}Cs_2$ | 75.9 | 55.5 (73.1) |
| ven- | (21) | $Mo_{12}P_2Ce_{0.5}Te_{0.5}Cs_2$ | 67.8 | 46.6 (68.7) |
| tion | (22) | $Mo_{12}P_2Ce_{0.5}La_{0.5}Cs_2$ | 77.0 | 55.1 (71.6) |
| | (23) | $Mo_{12}P_2Ce_{0.5}Nd_{0.5}Cs_2$ | 78.2 | 52.6 (67.3) |
| | (24) | $Mo_{12}P_2Ce_{0.5}Sm_{0.5}Cs_2$ | 76.1 | 52.0 (68.3) |

EXAMPLE 3

100 ml of each of the aforementioned catalysts Nos. (3), (6), (8), (9), (11), (12), (13), (C-1), (C-2), (C-3) and (C-4) was placed in a stainless steel reaction tube having an inside diameter of 2.5 cm and a length of 60 cm, and heated to 350° C. over a metal bath. A feed gas consisting of methacrolein, $O_2$, $N_2$, $H_2O$ and isobutylene in a molar ratio of 1:1.5:17.5:9.9:0.1 was passed through the catalyst layer for a contact time of 1.8 seconds (based on 0° C., 1 atmosphere) to carry out the reaction. The results obtained are illustrated in Table 3. The purity of methacrolein used was 99.5% by weight.

From the results, it is seen that when the feed gas contains isobutylene, the catalyst of the present invention exhibits catalytic activity equal to that exhibited when the feed gas does not contain isobutylene (see Table 1-1), while the control catalyst shows much inferior catalytic activity to that shown when the feed gas contains no isobutylene (see Table 1-2).

The same experiments on the catalyst wherein component B is Ag, Ga, Y, Ge, Te, La, Nd or Sm afforded practically the same results.

Table 3

| Catalyst No. | | Composition of catalyst (atomic ratio) | Conversion of methacrolein (%) | Per-pass yield (selectivity) of methacrylic acid (%) |
|---|---|---|---|---|
| | (3) | $Mo_{12}P_2Ce_{0.5}Be_{0.5}Cs_2$ | 76.1 | 57.6 (75.7) |
| Pre- | (6) | $Mo_{12}P_2Ce_{0.5}Sr_{0.5}Cs_2$ | 74.5 | 53.2 (71.4) |

Table 3-continued

| Catalyst No. | | Composition of catalyst (atomic ratio) | Conversion of methacrolein (%) | Per-pass yield (selectivity) of methacrylic acid (%) |
|---|---|---|---|---|
| sent | (8) | $Mo_{12}P_2Ce_{0.5}Zn_{0.5}Tl_2$ | 72.6 | 51.0 (70.2) |
| In- | (9) | $Mo_{12}P_2Ce_{0.5}Pb_{0.5}Rb_2$ | 71.3 | 51.9 (72.8) |
| ven- | (11) | $Mo_{12}P_2Ce_{0.5}Sb_{0.5}K_2$ | 70.5 | 49.1 (69.6) |
| tion | (12) | $Mo_{12}P_2Ce_{0.5}Bi_{0.5}Rb_2$ | 73.3 | 52.7 (71.9) |
|  | (13) | $Mo_{12}P_2Ce_{0.5}Cr_{0.5}Rb_2$ | 79.0 | 58.7 (74.3) |
|  | (C-1) | $Mo_{12}P_2Ce_{0.5}K_2$ | 49.1 | 24.9 (50.7) |
| Con- | (C-2) | $Mo_{12}P_2Ce_{0.5}Rb_2$ | 51.0 | 27.3 (53.5) |
| trol | (C-3) | $Mo_{12}P_2Ce_{0.5}Cs_2$ | 51.4 | 29.0 (56.4) |
|  | (C-4) | $Mo_{12}P_2Ce_{0.5}Tl_2$ | 53.3 | 27.8 (52.2) |

EXAMPLE 4

Methacrylic acid was produced from isobutylene in the manner described below by the first stage-second stage continuous method, to examine the effects of the unreacted isobutylene or other by-products contained in the first stage oxidation reaction mixture on the activity of the second stage oxidation catalyst.

(1) First stage oxidation catalyst

Bismuth nitrate (48.5 g), 116.5 g of cobalt nitrate, 29.1 g of nickel nitrate, 484.8 g of ferric nitrate and 10.1 g of potassium nitrate were added to 150 ml of water and dissolved with heating to make a solution (called solution A). Separately, 212 g of ammonium molybdate was dissolved with heating in 400 ml of water, and 5.76 g of 85% phosphoric acid was further added to form a solution (called solution B). While stirring solution A with heating, solution B was added thereto, and the mixture was evaporated to dryness while stirring it sufficiently. The dry matter was dried at 120° C. for 8 hours, and then calcined in a muffle furnace for 16 hours at 600° C. The resulting solid matter was pulverized and sifted to a size of 4 to 8 mesh. The product so obtained was used as the first stage oxidation catalyst, its composition being expressed as $Mo_{12}Bi_1Fe_{12}Co_4Ni_1P_{0.5}K_1$.

(2) Second stage oxidation catalyst

The aforementioned catalysts Nos. (3), (6), (8), (9), (11), (12), (13), (C-1), (C-2), (C-3) and (C-4) were each used as the second stage oxidation catalyst.

(3) First stage oxidation reaction 100 ml of the catalyst prepared in (1) above was packed into a stainless steel reaction tube having an inside diameter of 2.5 cm and a length of 60 cm, and heated to 340° C. over a metal bath. A feed gas consisting of isobutylene, air and steam in a molar ratio of 4:55:41 was passed through the catalyst layer at a space velocity of 2000 $hr^{-1}$. As a result, the conversion of isobutylene was 95.5%, the per-pass yield of methacrolein was 69.4%, the selectivity of methacrolein was 72.7%, and the proportion of the unreacted isobutylene and unsaturated hydrocarbons formed as by-products, which were contained in the reaction gas, was 7.3% based on the isobutylene fed. These results of the reaction were all calculated based on carbon. Other substances formed were tarry substances solidifying below 200° C., small amounts of methacrylic acid, acetic acid, acetone, furan, diacetyl, etc., and carbon dioxide and carbon monoxide.

(4) Second stage oxidation reaction 100 ml of the catalyst prepared for in (2) above was charged into a stainless steel reaction tube having an inside diameter of 2.5 cm and a length of 60 cm, and heated to 350° C. over a metal bath. The reaction mixture obtained by the first stage oxidation reaction of (3) above was immediately introduced to the catalyst layer, and passed therethrough. The results obtained are shown in Table 4.

From the results of Table 4, it is seen that in the production of methacrylic acid from isobutylene by the first stage-second stage continuous method, the catalyst of the present invention used as the second stage oxidation catalyst, even when the unreacted isobutylene or by-products are included in the first stage oxidation reaction mixture, shows catalytic activity which is virtually equal to that exhibited when they are not included in said mixture (see Example 1).

It is also seen that when the control catalyst is used as the second stage oxidation catalyst, on the other hand, its catalytic activity is greatly lowered by the unreacted isobutylene and by-products included in the first stage oxidation reaction mixture, and thus, the control catalyst is totally unsuitable for the first stage-second stage continuous method.

The same experiments on the catalyst in which the component B is Ag, Ga, Y, Ge, Te, La, Nd or Sm gave practically the same results.

Table 4

| Catalyst No. | | Composition of catalyst (atomic ratio) | Conversion of methacrolein (% | Per-pass yield (selectivity) of methacrylic acid (%) |
|---|---|---|---|---|
|  | (3) | $Mo_{12}P_2Ce_{0.5}Be_{0.5}Cs_2$ | 76.0 | 57.7 (75.9) |
| Pre- | (6) | $Mo_{12}P_2Ce_{0.5}Sr_{0.5}Cs_2$ | 74.3 | 53.0 (71.3) |
| sent | (8) | $Mo_{12}P_2Ce_{0.5}Zn_{0.5}Tl_2$ | 72.2 | 50.8 (70.4) |
| In- | (9) | $Mo_{12}P_2Ce_{0.5}Pb_{.5}Rb_2$ | 70.8 | 51.6 (72.9) |
| ven- | (11) | $Mo_{12}P_2Ce_{0.5}Sb_{0.5}K_2$ | 70.7 | 49.1 (69.4) |
| tion | (12) | $Mo_{12}P_2Ce_{0.5}Bi_{0.5}Rb_2$ | 73.1 | 52.5 (71.8) |
|  | (13) | $Mo_{12}P_2Ce_{0.5}Cr_{0.5}Rb_2$ | 79.1 | 58.5 (74.0) |
|  | (C-1) | $Mo_{12}P_2Ce_{0.5}K_2$ | 48.8 | 24.3 (49.8) |
| Con- | (C-2) | $Mo_{12}P_2Ce_{0.5}Rb_2$ | 50.9 | 27.0 (53.0) |
| trol | (C-3) | $Mo_{12}P_2Ce_{0.5}Cs_2$ | 51.1 | 28.0 (54.8) |
|  | (C-4) | $Mo_{12}P_2Ce_{0.5}Tl_2$ | 53.1 | 27.5 (51.8) |

EXAMPLE 5

The oxidation reaction of acrolein was carried out under the same conditions as in Example 1, except for the use of a feed gas consisting of acrolein, $O_2$, $N_2$ and $H_2O$ in a molar ratio of 1:2:8:9. The catalyst used was the aforementioned catalyst No. (3) or (13).

The use of catalyst No. (3) resulted in an acrolein conversion of 93.8% and an acrylic acid yield of 83.7% (an acrylic acid selectivity of 89.2%. The use of catalyst No. (13), on the other hand, resulted in an acrolein conversion of 95.6% and an acrylic acid yield of 85.3% (an acrylic acid selectivity of 89.2%).

When the same reaction was performed using a feed gas consisting of acrolein, $O_2$, $N_2$, $H_2O$ and propylene in a molar ratio of 1:2:8:8.9:0.1, neither of the catalysts showed a substantial reduction in its catalytic activity, though propylene was present in the feed gas.

What we claim is:

1. A process for preparing unsaturated carboxylic acids, which comprises catalytically oxidizing unsaturated aldehydes in the vapor phase using molecular oxygen in the presence of a catalyst expressed by the formula $$A_a B_b Ce_c Mo_d P_e O_f$$

wherein A represents at least one element selected from K, Rb, Cs and Tl; B represents at least one of Be, Sr, Pb, Cr, Ag, Ca, Y, Ge, Te, La, Nd or Sm; a, b, c, d, e, and f are the number of the atoms of A, B, Ce, Mo, P and O, respectively; and when d is 12, a, b, c and e are independently 0.05 to 12, and f is the number of oxygen atoms which satisfies the valences of the other elements.

2. The process of claim 1 wherein the unsaturated aldehyde is acrolein.

3. The process of claim 1 wherein the unsaturated aldehyde is methacrolein.

4. The process of claim 1 wherein the reaction is carried out at a temperature of 250° to 500° C.

5. The process of claim 1 wherein the reaction is carried out in the presence of an inert gas.

* * * * *